US006204289B1

(12) United States Patent
Eterovic et al.

(10) Patent No.: US 6,204,289 B1
(45) Date of Patent: Mar. 20, 2001

(54) CEMBRANOID INHIBITORS OF NICOTINIC ACETYLCHOLINE RECEPTORS

(76) Inventors: Vesna A. Eterovic, Box 60-327, Bayamon, PR (US) 00960-6032; Abimael D. Rodriguez, P.O. Box 23346, UPR Station, U.P.R. Dept. of Chemistry, San Juan, PR (US) 00931-3346; Richard M. Hann, Box 60-327, Bayamon, PR (US) 00960-6032; Pedro A. Ferchmin, Box 60-327, Bayamon, PR (US) 00960-6032; One R. Pagan, Box 60-327, Bayamon, PR (US) 00963-6032; Misty J. Eaton, Box 60-327, Bayamon, PR (US) 00960-6032

( * ) Notice: Subject to any disclaimer, the term of this patent is extended or adjusted under 35 U.S.C. 154(b) by 0 days.

(21) Appl. No.: 09/092,407

(22) Filed: Jun. 4, 1998

Related U.S. Application Data

(60) Provisional application No. 60/048,647, filed on Jun. 5, 1997.

(51) Int. Cl.$^7$ ........................ A61K 31/045; A61K 31/215
(52) U.S. Cl. ........................ 514/451; 514/460; 514/461; 514/470; 514/475; 514/813
(58) Field of Search ................... 514/451, 460, 514/461, 470, 475, 813

(56) References Cited

U.S. PATENT DOCUMENTS 4,906,794 * 3/1990 Umezu et al. ................ 568/821
5,039,671 * 8/1991 Baggiolini et al. ............ 514/167

FOREIGN PATENT DOCUMENTS 0 258 082 A2  3/1988  (EP) .
0 271 387 A3  6/1988  (EP) .

OTHER PUBLICATIONS

Vesna A. Eterovic et al., "Diterpenoids from Caribbean Gorgonians Act as Noncompetitive Inhibitors of the Nicotinic Acetylcholine Receptor", Cellular and Molecular Neurobioloby, vol. 13, No. 2, 1993, pp. 99–110.

Vesna A. Eterovic et al., "The Ion Channel of Muscle and Electric Organ Acetylcholine Receptors: Differing Affinities for Noncompetitive Inhibitors", Cellular and Molecular Neurobiology, vol. 13, No. 2, 1993, pp. 111–121.

R.M. Hann, et al., "Affinities of New Cembranoids for the Nicotinic Acetylcholine Receptor", Soc. Neurosci., vol. 21, 1995, p. 605, XP–002080454, (Abstract).

Database WPI, Section Ch. Week 9533, Derwent Publications Ltd., London, GB; Class B02, AN 95–248265, XP–002080455 (Abstract). (1995).

Hann et al., 1998, "Characterization of Cembranoid Interaction with the Nicotonic Acetylcholine Receptor," *Journal of Pharmacology and Experimental Therapeutics*, vol. 287, No. 1, pp. 253–260.

Eaton et al., 1998, "$\beta_{T10'A}$ and $\beta_{T10'I}$ Mutations in the M2 Region of Nicotinic Receptors Alter the Potency of Phencyclidine, But Not The Cembranoid Pseudoplexauric Acid Methyl Ester," Soc. Neurosci. Abstr., 24:84.

Eterovic et al., 1994, "Cembranoids Inhibit Neuronal Acetylcholine Receptors," Soc. Neurosci. Abstr., vol. 20, p. 842 (Miami, Florida).

Eaton et al, Dec. 5, 1998, "$\beta_{T10'A}$ and $\beta_{T10'I}$ Mutations in the M2 Region of Nicotinic Receptors Alter the Potency of Phencyclidine, But Not The Cembranoid Pseudoplexauric Acid Methyl Ester," 7$^{th}$ Puerto Rico Neuroscience Conference (Bayamon, PR).

Nicolau et al., 1998, "Behavioral Effects of Cembranoids: Evidence of In Vivo Central Nicotinic Action," 7$^{th}$ Puerto Rico Neuroscience Conference (Bayamon, PR).

Pagan et al., 1998, "A Model for the Relationship Between the Local Anesthetic, General Anesthetic and Cembranoid Binding Sites on the Torpedo Nicotinic Acetylcholine Receptor," 7$^{th}$ Puerto Rico Neuroscience Conference (Bayamon, PR).

Hann et al., 1994, "Further Characterization of How Cembranoids Inhibit the Acetylcholine Receptor," International Symposium, The Cholinergic Synapse (Baltimore, MD).

Lu et al., 1993, "New Cembranoid Inhibitors of the Nicotinic Acetylcholine Receptor: Structure–Function Relationships," 2$^{nd}$ Puerto Rico Neuroscience Conference (San Juan, PR).

Eterovic et al., 1993, "Effect of Cembranoids on Neuronal Acetylcholine Receptors," 2$^{nd}$ Puerto Rico Neuroscience Conference (San Juan, PR).

Hann et al., 1993, "The Biological Actions of Gorgonian Cembranoids on the Central Nervous System and the Peripheral Acetylcholine Receptor," Marine Natural Products: Chemical Structure and Bioactivity (Lajas, PR).

Hann et al., 1993, "The Acetylcholine Receptor: Binding Sites for Competitive and Non–Competitive Inhibitors," Joint EPSCOR and AAAS Annual Meeting (Mayaguez, PR).

Pagan et al., Apr. 23–25, 1993, "Inhibition of ['H]Phencyclidine Binding to the Nicotinic Acetylcholine Receptor by Cembranoids from Gorgonians," 9$^{th}$ Student Research Congress (San Juan, PR).

Eterovic et al., 1992, "Differences in the Action of Non-competitive Inhibitors on Muscle and Electric Organ Acetylcholine Receptors," Keystone Symposium of Synapse Formation and Function (Big Sky, MN).

(List continued on next page.)

*Primary Examiner*—Frederick Krass
(74) *Attorney, Agent, or Firm*—Patent Law Offices of Heath W. Hoglund

(57) ABSTRACT

The present invention relates to the use of cembranoids to inhibit nicotinic acetylcholine receptors.

20 Claims, 1 Drawing Sheet

OTHER PUBLICATIONS

Figure 1:
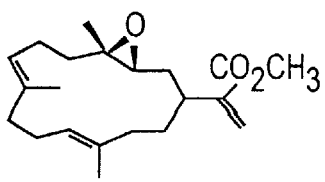
Figure 1:
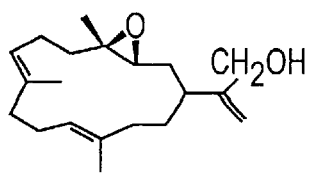
Figure 1:
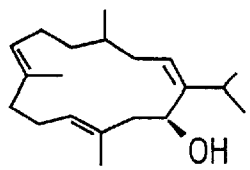
Figure 1:
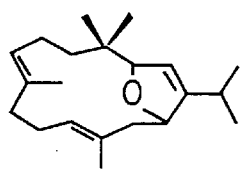
Figure 1:
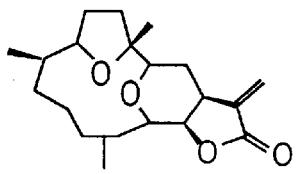
Figure 1:
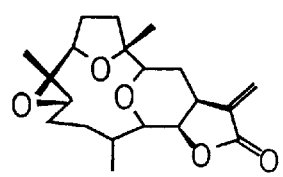
Figure 1:
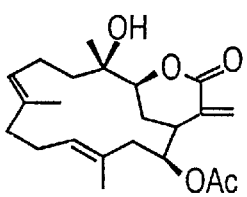
Figure 1:
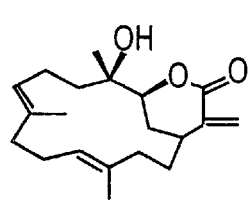
Figure 1:
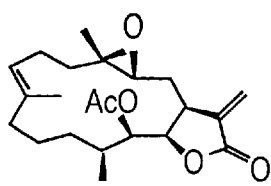
Figure 1:
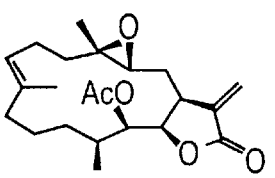
Figure 1:
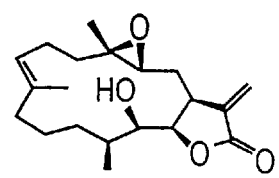
Figure 1:
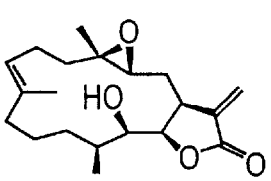
Figure 1:
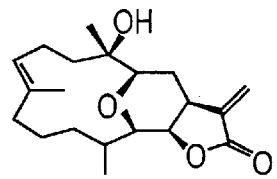
Figure 1:
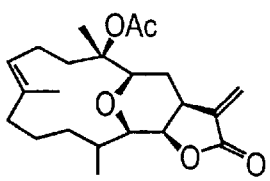
Figure 1:
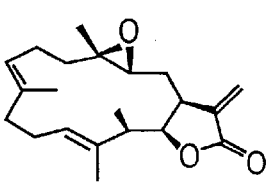
Figure 1:
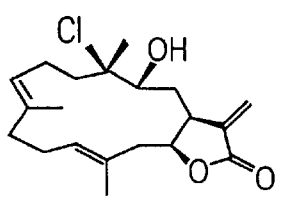
Figure 1:
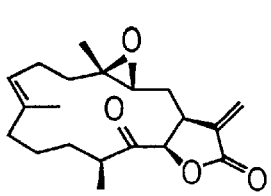

Eterovic et al., 1991, "Caribbean Cembranoids are Noncompetitive Inhibitors of the Nicotinic Acetylcholine Receptor," Joint EPSCOR and AAAS Annual Meeting (San Juan, PR).

Eterovic et al., 1992, "Cembranoids from Eunicea: A New Group of Noncompetitive Inhibitors of the Nicotinic Acetylcholine Receptor (AChR)," Biophysical Society (Houston, TX).

R. M. Hahn et al., "Affinities of Gorgonian Cembranoids for the Phencyclidine High–Affinity Binding Site on the Nicotinic Acetylcholine Receptor," *Joint EPSCoR and AAAS Annual Meeting*, Dorado, P.R., Apr. 28–29, 1995.

R. M. Hahn et al., "The Gorgonian Cembranoid Binding Site on the Nicotine Acetylcholine Receptor," *5th International Symposium on Neurotoxins in Neurobiology*, Mayaguez, P.R., Aug. 31–Sep. 5, 1995.

V.A. Eterovic et al., "The Nicotinic Acetylcholine Receptor: Inhibitor Tales," *X Reunion Anual de la Sociedad Argentine de Neuroquimica*, Bahia Blanca, Argentina, Oct. 19–21, 1995.

O. R. Pagan et al., "Inhibition [$^3$H]–Phencyclidine Binding to the Nicotinic Acetylcholine Receptor by Gorgonian–erived Diterpenoids," *4th Puerto Rico Neuroscience Conference*, San Juan, Puerto Rico, Dec. 9, 1995.

R. M. Hahn et al., "Gorgonian Cembranoids from Puerto Rico as Noncompetitive Inhibitors of the Nicotinic Acetylcholine Receptor," *National Minority Research Symposium*, Miami, Florida, Nov. 13–17, 1996.

R. M. Hahn et al., "Hydrophobicity as an Affinity Factor for Cembranoid binding to the Nicotine Acetylcholine Receptor," *5th Puerto Rico Neuroscience Conference*, San Juan, P.R., Dec. 14, 1996.

V. A. Eterovic et al., "The Noncompetitive Inhibitors Domain of the Nicotinic Acetylcholine Receptor," *Neuroscience Symposium and Program Directors Meeting*, Tallahassee, Florida, Mar. 5–8, 1997.

P. A. Ferchmin et al., "Coral and Tobacco Cembranoids Inhibit the Expression of Nicotine Sensitization of Exploratory Activity in Rats," *Society for Neuroscience Annual Meeting*, 1999.

O. R. Pagan et al., "Mutally–Exclusive Binding of Anesthetic Agents and Gorgonian Cembranoids to the Nicotinic Acetylcholine Receptor," *Society for Neuroscience Annual Meeting*, Los Angeles, California, Nov. 7–12, 1998.

V. A. Eterovic et al., "Cembranoids Inhibit Neuronal Acetylcholine Receptors," *Society for Neuroscience Annual Meeting*, Miami Beach, Florida, Nov. 13–18, 1994.

R. M. Hahn et al., "The α–Conotoxins GI and MI Distinguish between the Nicotinic Acetylcholine Receptor Agonist Sites while DI Does Not," *Biochemistry*, vol. 33, No. 47, 1994, pp. 14058–14063.

\* cited by examiner

1. METHYLPSE-
UDOPLEXAURATE

2. PSEUDOPLEXAUROL

3. SARCOPHYTOL-A

4. MARASOL

5. INOLIDE-A

6. INOLENE OXIDE

7. CRASSIN ACETATE 8. 14-DEOXYCRASSIN

9. EUPALMERIN ACETATE 10. 12,13-BISEPI-
EUPALMERIN ACETATE 11. 12,13-BISEPI-
EUPALMERIN

12. EUPALMERIN

13. EUNICIN

14. EUNICIN ACETATE

15. EUNIOLIDE

16. CHLOROEUNIOLIDE

17. EUPALMERONE

CEMBRANOID INHIBITORS OF NICOTINIC ACETYLCHOLINE RECEPTORS

STATEMENT OF RELATED APPLICATIONS

This application claims the benefit of provisional application No. 60/048,647, filed Jun. 5, 1997, which is herein specifically incorporated by reference.

BACKGROUND OF THE INVENTION

Nicotinic acetylcholine receptors (AchRs) are proteins that control skeletal muscle contraction, sympathetic and parasympathetic ganglia function (which is related to the control of the cardiovascular and visceral functions) and important communication pathways in the brain. These receptors are disturbed in the Alzheimer's and Parkinson's diseases, schizophrenia and other disorders involving memory loss, cognitive problems and/or dementia (2,14,15). Neuronal AchRs are the biological substrate for nicotine addiction (3–6, 17). Blockade of these receptors could contribute to the anti-addictive properties of certain alkaloids (1).

Inhibitors of AchRs affect all these processes and many are used for therapeutic purposes. These inhibitors form a large, chemically-heterogenous group of compounds, which block the receptor by a variety of mechanisms (15).

We discovered a new family of AchR inhibitors, the cembranoids isolated from gorgonian corals (see the 'Detailed Description of the Invention'). Some aspects of this discovery were reported in the literature (7–13, 16, 18, 19).

To our knowledge, there are no other patents related to the use of cembranoids as inhibitors of AChRs.

SUMMARY OF THE INVENTION

Cembranoids are cyclic diterpenoids naturally present in many plants and invertebrate animals. We discovered that cembranoids inhibit both peripheral and neuronal AchRs at concentrations ranging from $10^{-15}$ molar to $10^{-4}$ molar; cembranoids also increase the rate of receptor desensitization. Seventeen different cembranoid analogs were tested. There are two main differences between previously known AchR inhibitors and these new cembranoid inhibitors. First, two of the new inhibitors (eupalmerin acetate and pseudoplexauric acid) are more potent than any previously known inhibitors by a factor of at least 1000; therefore, less side effects would be expected in any potential therapeutic application. Second, cembranoids are present in tobacco leaves, and therefore potentially have an effect on nicotine action in the brains of cigarette smokers. Nicotine-induced desensitization of neuronal acetylcholine receptors is related to behavioral tolerance or addiction to nicotine (6); since cembranoids increase receptor desensitization, they are likely to increase tobacco addictive properties. Thus, by extracting the cembranoids from tobacco, this could produce less addictive cigarettes (or any tobacco related product). On the other hand, addition of cembranoids to tobacco could possibly increase its addictive properties. In addition, cembranoids displace general anesthetics from the muscle-type AchR, and so they could ameliorate the undesirable side-effects of anesthesia in patients with Myasthenia gravis.

DRAWINGS

FIG. 1 depicts the chemical structures of some of the cembranoids of the invention.

DETAILED DESCRIPTION OF THE INVENTION

Cembranoids are cyclic diterpenoids containing the 14-carbon cembrane ring, substituted with one or more oxygen-containing groups (see FIG. 1). These compounds are natural products present in many terrestrial plants and marine invertebrates (20).

We discovered that cembranoids isolated from gorgonian-corals inhibit both peripheral and neuronal AchRs.

EXAMPLE 1

Peripheral AchRs: Receptors from mammalian skeletal muscle (embrionary form) and the electric organ from fish (*Torpedo californica*) were expressed in *Xenopus laevis* oocytes and studied with the voltage clamp technique. With both receptors, cembranoids decrease the amplitude of ACh-induced currents with affinities ranging from $10^{-15}$ to $10^{-5}$ M. The inhibition by cembranoids is reversible, noncompetitive, independent of membrane potential (−80 to +20 mV) and accompanied by an increase in the rate of desensitization. In binding assays with electric organ membranes, cembranoids competitively and completely inhibited $^3$H-phencyclidine (PCP) binding to desensitized AchR, with dissociation constants ranging from $10^{-7}$ to $10^{-4}$ M. This confirmed that cembranoids, as phencyclidine, are noncompetitive inhibitors of the AchR. The minimum molecular features for cembranoid high-affinity binding are the cembrane ring and a single hydroxy group on carbon 14; this suggests that these molecules interact primarily with hydrophobic residues on the AchR.

Cembranoids also displace the general anesthetic octanol from its binding site. This observation suggests that cembranoids could ameliorate the undesirable side-effects of any general anesthesia such as in patients with Myasthenia gravis.

EXAMPLE 2

Neuronal AchRs: Cembranoids inhibit nicotinic neurotransmission in rat superior cervical ganglion. Cembranoids also inhibit three subtypes of neuronal AchRs from rat brain, the α4β2, α3β2 and α2β2 receptors expressed in oocytes. The main effect of cembranoids on neuronal receptors was an increase in the rate of desensitization; this effect was caused by an increase in the amplitude of fast desensitization at the expense of slow desensitization.

Most noncompetitive inhibitors of the AChR affect other ion channels as well. In other words, they are not very specific. In contrast, the cembranoids had no effect on glutamatergic or gabaergic neurotransmission in the hippocampus which shows that they do not act upon the glutamate or GABA receptors, sodium channels or calcium channels found in hippocampal neurons. Hence, cembranoids are a more specific class of noncompetitive inhibitors for the AchR.

Reference

The following references, and any other references set forth in the specification, are herein incorporated by reference.
1. Badio et al., "Ibogaine: a potent noncompetitive blocker of ganglionic/neuronal nicotinic receptors," Mol. Pharmacol; 51:1–5 (1997).
2. Benowitz N. L., "Pharmacology of nicotine: addiction and therapeutics," Annu. Rev. Pharmacol. Toxicol.; 36:597–613 (1996).
3. Brioni J. D. et al., "Anxiolytic-like effects of the novel cholinergic channel activator ABT-418," J. Pharmacol, Exp. Therap; 271,353–361 (1994).
4. Chessell I. P., "Acetylcholine receptor targets on cortical pyramidal neurones as targets for Alzheimer's therapy," Neurodegeneration; 5:453–459 (1996).

5. Clarke P. B. S., "Nicotine dependence-mechanisms and therapeutic strategies," Biochem, Soc. Symp; 59:83–95 (1994).
6. Collins A. C. and Marks M. J., "Are nicotinic receptors activated or inhibited following chronic nicotine treatment?" Drug Development Research; 38,231–242 (1996).
7. Eterovic V. A., Hann R. M., Ferchmin P. A., Rodriguez A. D., Li L., Lee Y. H., and McNamee M. G., "Diterponoids from Caribbean gorgonians act as noncompetitive inhibitors of the nicotinic acetylcholine receptor," Cell. Mol. Neurobiol.; 13:99–110 (1993).
8. Eterovic V. A., Li L., Ferchmin P. A., Lee Y. H., Hann R. M., Rodriguez A. D., and McNamee M., "The ion channel of muscle and electric organ acetylcholine," Cell. Mol. Neurobiol; 13:111–3 (1993).
9. Hann R. M., Pagan Ojeda O. R., Rodriguez A. D. and Eterovic V. A., "Affinities of gorgonian cembranoids for the phencyclidine high-affinity binding site on the nicotinic acetylcholine receptor," Joint EPSCOR and AAAS Annual Meeting (Dorado, PR) (1995).
10. Hann R. M., Pagan Ojeda O. R., Rodriguez A. D., and Eterovic V. A., "The Gorgonian cembranoid binding site on the nicotinic acetylcholine receptor," 5th International Symposium on Neurotoxins in Neurobiology, (Mayaguez, P.R.) (1995).
11. Hann R. M., Pagan O. R., Rodriguez A. D. and Eterovic V. A., "Affinities of new cembranoids for the nicotinic acetylcholine receptor," Soc. Neurosci. Abstr. Vol. 21, abs.4; 247.6, p. 605 (San Diego, Calif.) (1995).
12. Hann R. M., Pagan O. R., Jacome T., Gregory L., and Eterovic V. A., "Gorgonian cembranoids from Puerto Rico as noncompetitive inhibitors of the nicotinic acetylcholine receptor," National Minority Research Symposium (Miami, Fla.) (1996).
13. Hann R. M., Pagan O. R., Jacorne T., Gregory L., Rodriguez A. D., and Eterovic V. A., "Hydrophobicity as an affinity factor for cembranoid binding to the nicotinic acetylcholine receptor," 5th Puerto Rico Neuroscience Conference (San Juan, P.R.) (1996).
14. James J. R., and Nordberg A., "Genetic and environmental aspects of the role of nicotinic receptors in neurodegenerative disorders: emphasis on Alzheimer's dosease and Parkinson's disease," Behavioral Genetics; 25:149–159 (1995).
15. Leonard S. et al., "Nicotinic receptor function in schizophrenia," Schizophrenia Bulletin; 22:431–445 (1996).
16. Lu R., Pagan O. R., Flann R. M., Rodriguez A. D., and Eterovic V. A., "New cembranoid inhibitors of the nicotinic acetylcholine receptor: structure-function relationships," Puerto Rico Neuroscience Conference, (San Juan, PR). (1993)
17. Ochoa E. L. M., "Nicotine-related brain disorders: the neurobiological basis of nicotine dependence," Cel. Mol. Neurobiol.;14:195–225 (1994).
18. Pagan O. R., Hann R. M., Rodriguez A. D., and Eterovic V. A., "Inhibition of [¹H]phencyclidine binding to the nicotinic acetylcholine receptor by cembranoids from gorgonians," 9th Student Research Congress (San Juan, PR). (1993)
19. Pagan O. R., Hann R. M., Vergara A., Rodriguez A. D., and Eterovic V. A., "Inhibition of [¹H]-phencyclidine binding to the nicotinic acetylcholine receptor by Gorgonian-derived diterpenoids," 4th Puerto Rico Neuroscience Conference (San Juan, PR). (1995)
20. Rodriguez A. D., "The natural products chemistry of west indian Gorgonian octocorals," Tetrahedron; 51:4571–4618 (1995).

We claim:
1. A method of inhibiting at least one nicotinic acetylcholine receptor, said method comprising administering to a host in need of said inhibiting a cembranoid, wherein said at least one cembranoid is administered in an amount sufficient to achieve a concentration, within said host, of approximately $10^{-8}$ to $10^{-15}$ molar.
2. The method of claim 1, wherein the at least one cembranoid is selected from the group consisting of:

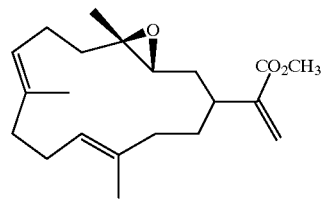

1. METHYLPSEUDO-PLEXAURATE

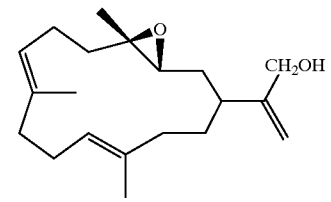

2. PSEUDOPLEXAUROL

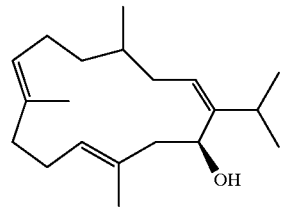

3. SARCOPHYTOL-A

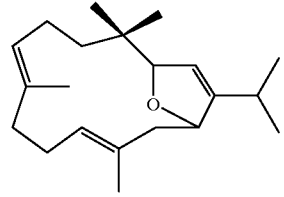

4. MARASOL

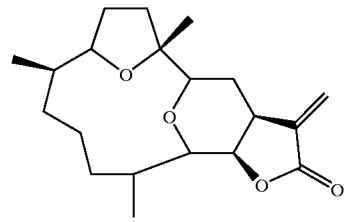

5. INOLIDE-A

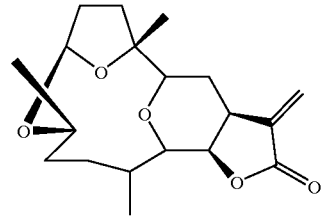

6. INOLENE OXIDE

-continued

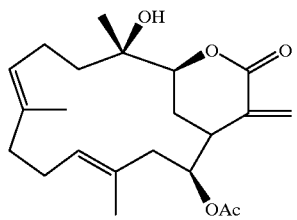

7. CRASSIN ACETATE

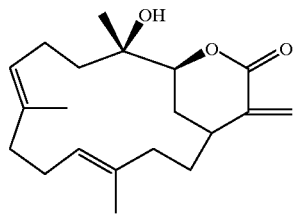

8. 14-DEOXYCRASSIN

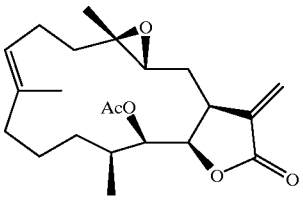

9. EUPALMERIN ACETATE

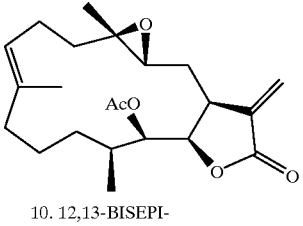

10. 12,13-BISEPI-
EUPALMERIN ACETATE

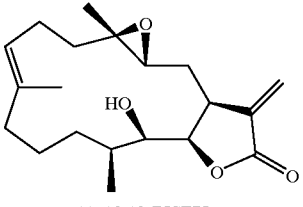

11. 12,13-BISEPI-
EUPALMERIN

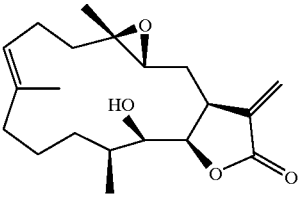

12. EUPALMERIN

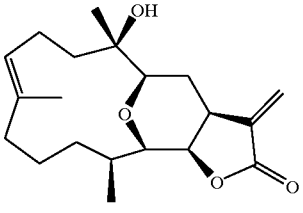

13. EUNICIN

-continued

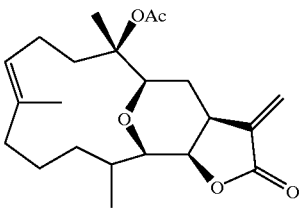

14. EUNICIN ACETATE

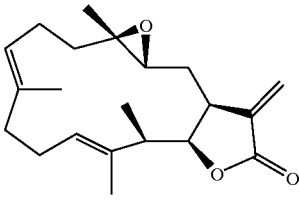

15. EUNIOLIDE

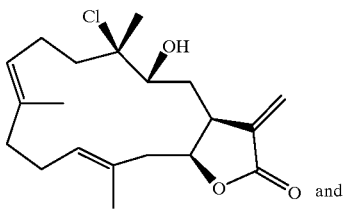

16. CHLOROEUNIOLIDE and

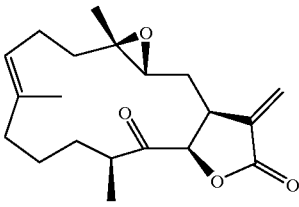

17. EUPALMERONE

3. The method of claim 1, wherein more than one cembranoid is administered.

4. The method of claim 1, wherein the nicotinic acetylcholine receptor is a neuronal receptor.

5. The method of claim 4, wherein the neuronal receptor is an $\alpha 4\beta 2$, $\alpha 3\beta 2$, or $\alpha 2\beta 2$ receptor.

6. The method of claim 1, wherein the nicotinic acetylcholine receptor is a skeletal muscle receptor.

7. The method of claim 1, wherein said method ameliorates the undesirable side-effects of anesthesia in a host with myasthenia gravis.

8. The method of claim 1, wherein said at least one cembranoid is eupalmerin acetate.

9. The method of claim 1, wherein said at least one cembranoid is methylpseudoplexaurate.

10. The method of claim 1, wherein the concentration of cembranoid within the host is approximately $10^{-15}$ molar.

11. A method of treating a disorder involving memory loss, cognitive problems, and/or dementia, said method comprising administering to a host in need of said treating at least one cembranoid, wherein said at least one cembranoid is administered in an amount sufficient to achieve a concentration, within the host, of approximately $10^{-8}$ to $10^{-15}$ molar.

12. The method of claim 11, wherein more than one cembranoid is administered.

13. The method of claim 11, wherein the disorder is Alzheimer's disease, Parkinson's disease, or schizophrenia.

14. The method of claim 13, wherein the disorder is Alzheimer's disease.

15. The method of claim 13, wherein the disorder is Parkinson's disease.

16. The method of claim 13, wherein the disorder is schizophrenia.

17. The method of claim 11, wherein said at least one cembranoid is selected from the group consisting of:

1. METHYLPSEUDOPLEXAURATE

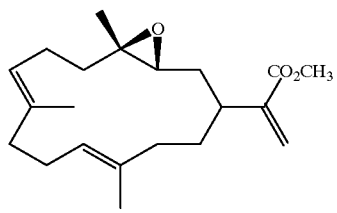

2. PSEUDOPLEXAUROL

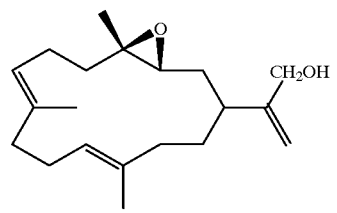

3. SARCOPHYTOL-A

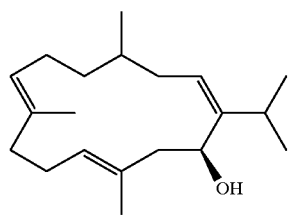

4. MARASOL

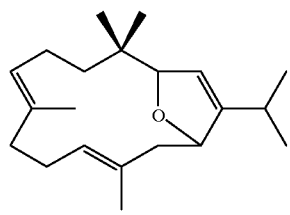

5. INOLIDE-A

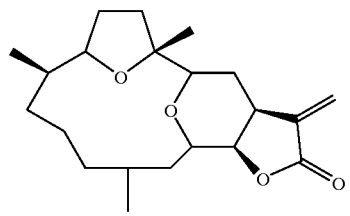

6. INOLENE OXIDE

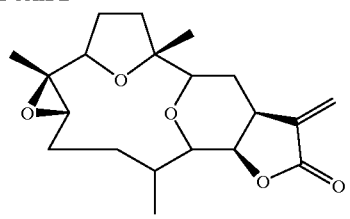

-continued

7. CRASSIN ACETATE

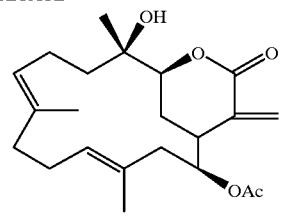

8. 14-DEOXYCRASSIN

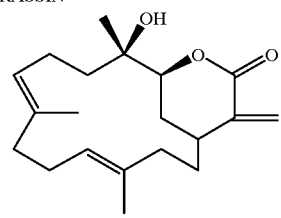

9. EUPALMERIN ACETATE

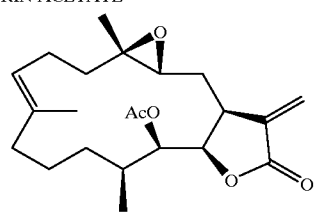

10. 12,13-BISEPIEUPALMERIN ACETATE

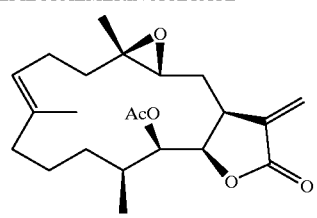

11. 12,13-BISEPIEUPALMERIN

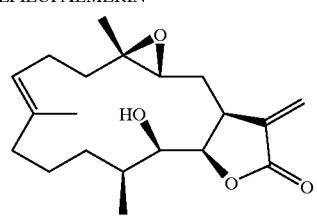

12. EUPALMERIN

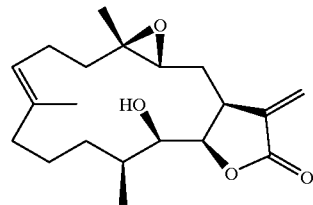

13. EUNICIN
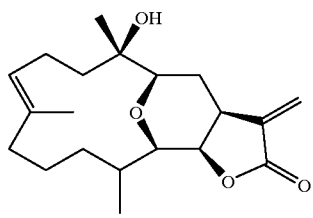
14. EUNICIN ACETATE
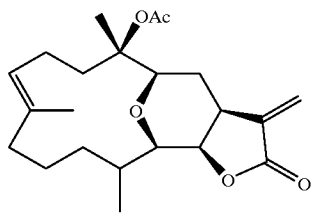
15. EUNIOLIDE
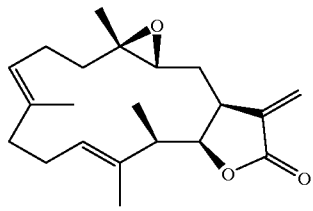
16. CHLOROEUNIOLIDE
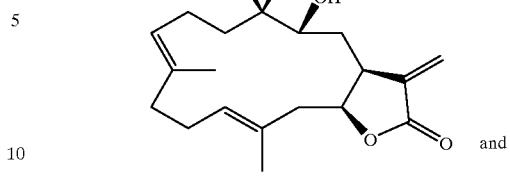
and
17. EUPALMERONE
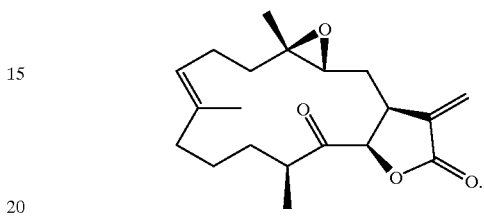
18. The method of claim 11, wherein said at least one cembranoid is eupalmerin acetate.
19. The method of claim 11, wherein said at least one cembranoid is methylpseudoplexaurate.
20. The method of claim 11, wherein the concentration of cembranoid within the host is approximately $10^{-15}$ molar.
* * * * *